US00PP11486P

United States Patent [19]

Trees

[11] Patent Number: Plant 11,486

[45] Date of Patent: Aug. 22, 2000

[54] NEW GUINEA IMPATIENS PLANT NAMED 'BFP-796'

[75] Inventor: Scott C. Trees, Nipomo, Calif.

[73] Assignee: Ball FloraPlant, a division of Ball Horticultural Company, West Chicago, Ill.

[21] Appl. No.: 09/112,648

[22] Filed: Jul. 9, 1998

[51] Int. Cl.[7] ..... A01H 5/00

[52] U.S. Cl. ..... Plt./318

[58] Field of Search ..... Plt./318

[56] References Cited

U.S. PATENT DOCUMENTS

P.P. 10,108 11/1997 Trees ..... Plt./318

*Primary Examiner*—Howard J. Locker
*Assistant Examiner*—Kent L. Bell
*Attorney, Agent, or Firm*—C. A. Whealy

[57] ABSTRACT

A new and distinct cultivar of New Guinea Impatiens plant named 'BFP-796', characterized by its large and numerous orange-colored flowers; upright and mounded plant habit; short internodes; good basal branching; and dark green leaves.

1 Drawing Sheet

BACKGROUND OF THE INVENTION

The present invention relates to a new and distinct cultivar of New Guinea Impatiens plant, botanically known as *Impatiens hawkeri,* and hereinafter referred to by the cultivar name 'BFP-796'.

The new New Guinea Impatiens is a product of a planned breeding program conducted by the Inventor in Arroyo Grande, Calif. The objective of the breeding program was to develop new cultivars with excellent basal branching, upright and medium growth habit, numerous large flowers, and interesting flower and foliage colors.

The new cultivar originated from a cross made by the Inventor to two unidentified proprietary *Impatiens hawkeri* selections. The cultivar 'BFP-796' was discovered and selected by the Inventor as a flowering plant within the progeny of the stated cross in a controlled environment in Arroyo Grande, Calif., on Sep. 15, 1996.

Asexual reproduction of the new cultivar by terminal cuttings taken at Arroyo Grande, Calif., has shown that the unique features of this new Impatiens are stable and reproduced true to type in successive generations of asexual reproduction.

SUMMARY OF THE INVENTION

The following traits have been repeatedly observed and are determined to be the unique characteristics of 'BFP-796'. These characteristics in combination distinguish 'BFP-796' as a new and distinct cultivar:

1. Large and numerous orange-colored flowers.
2. Upright and mounded plant habit.
3. Short internodes.
4. Good basal branching.
5. Dark green leaves.

The new New Guinea Impatiens can be compared to the commercial cultivar, 'BSR-195 Salmon' (disclosed in U.S. Plant Pat. No. 8,870). However, in side-by-side comparisons conducted by the Inventor in Arroyo Grande, Calif., plants of the new New Guinea Impatiens differ from plants of the cultivar 'BSR-195 Salmon' in the following characteristics:

1. Plants of the new New Guinea Impatiens are more compact and have shorter lateral branches than plants of the cultivar 'BSR-195 Salmon'.

2. Under high light conditions, leaves of plants of the cultivar 'BSR-195 Salmon' will become variegated whereas leaves of plants of the new New Guinea Impatiens will maintain solid dark green color.

3. Flowers of plants of the new New Guinea Impatiens are more orange in color than flowers of plants of the cultivar 'BSR-195 Salmon'.

4. Plants of the new New Guinea Impatiens have longer peduncles than plants of the cultivar 'BSR-195 Salmon'.

A detailed comparison of plants of the cultivar 'BFP-796' and the cultivar 'BSR-195 Salmon' appears in Chart A at the end of the specification.

BRIEF DESCRIPTION OF THE PHOTOGRAPH

The accompanying colored photograph illustrates the overall appearance of the new cultivar, showing the colors as true as it is reasonably possible to obtain in colored reproduction of this type. The photograph comprises a top perspective view of a typical plant of 'BFP-796'. Flower and foliage colors in the photograph appear lighter than the actual colors due to light reflectance.

DETAILED BOTANICAL DESCRIPTION

The cultivar 'BFP-796' has not been observed under all possible environmental conditions. The phenotype may vary somewhat with variations in environment such as temperature and light intensity, without, however, any variance in genotype. The following observations, measurements and comparisons describe plants grown in 10-cm pots in Arroyo Grande, Calif., under commercial practice in a glass-covered greenhouse with day temperatures about 22° C. and night temperatures about 18° C.

In the following description, color references are made to The Royal Horticultural Society Colour Chart except where general terms of ordinary dictionary significance are used.

Botanical classification: *Impatiens hawkeri* cultivar 'BFP-796'.

Parentage:

*Male parent.*—Unidentified proprietary *Impatiens hawkeri* selection.

*Female parent.*—Unidentified proprietary *Impatiens hawkeri* selection.

Propagation:

*Type cutting.*—Terminal cuttings.

*Time to initiate roots.*—About 7 days at temperatures about 18° C.

*Time to develop roots.*—About 21 days at temperatures about 18° C.

*Rooting habit.*—Fibrous, fine, freely branching.

Plant description:

*Plant form.*—Upright and mounded.

*Growth and branching habit.*—Moderately vigorous. Good basal branching with about six lateral branches at the base, dense and bushy growth. Appropriate for 10 and 12.5-cm containers.

*Plant height.*—About 12.6 cm.

*Crop time.*—About eight weeks are required to produce a finished flowering plant in a 10-cm container from a rooted cutting.

*Lateral branches.*—Length: About 6 cm. Diameter: About 6 mm. Internode length: About 2 cm. Color: 144C.

*Foliage description.*—Leaves simple, generally symmetrical, abundant, in whorls or opposite. Quantity of leaves per lateral branch: About nine. Length: About 9 cm. Width: About 3.2 cm. Shape: Lanceolate with acuminate apex, attenuate base and ciliate and serrate margin. Texture: Rugose, slightly pubescent. Color: Fully expanded foliage, upper surface: 137A. Fully expanded foliage, lower surface: 147B. Venation, upper surface: 145C. Venation, lower surface: 145C. Petiole: Length: About 1.5 cm. Diameter: About 3 mm. Color: 145C.

Flower description:

*Flower type and habit.*—Large orange-colored flowers. Freely and continuously flowering. Flowers arise from leaf axils. Usually about nine flowers and flower buds per lateral branch. Flowers positioned mostly above the foliage and typically face outward to upward. Flowers generally flat and rounded. Flowers persistent.

*Flowering season.*—Year-round under greenhouse conditions. In the garden, flowering is continuous from spring until fall.

*Flower longevity.*—About 3 or 4 days.

*Flower size.*—Diameter: About 7.5 cm. Depth: About 1.5 cm.

*Flower buds.*—Length: About 2.5 cm. Diameter: About 1.5 cm. Shape: Ovoid, pointed. Color: 41B.

*Petals.*—Quantity: Five, overlapping. Length: About 3 cm. Width: About 3.5 cm. Shape: Obcordate with emarginate apex, attenuate base and entire margin. Texture: smooth, iridescent. Color: When opening, upper surface: 40A. When opening, lower surface: 41B. Fully opened, upper surface: 40B with 51A at base. Fully opened, lower surface: 38B. Upper surface fading to: 39A.

*Spur.*—Length: About 6.6 cm. Shape: Narrow and curved. Color: 53C.

*Peduncles.*—Length: About 5.6 cm. Angle: About 45° to the lateral branch. Strength: Moderately strong. Color: 144D.

*Reproductive organs.*—Androecium: Stamen number: Five, anthers fused, filaments free. Anther shape: Obovate. Anther color: 12D. Amount of pollen: Moderate. Pollen color: 13D. Gynoecium: Five-loculate fused. Gynoecium color: 143C.

Disease resistance: Under commercial conditions, resistance to pathogens has not been observed.

Seed development: Seed production has not been observed.

CHART A

| CHARACTERISTIC | 'BFP-796' | 'BSR-195 SALMON' |
|---|---|---|
| PLANT HEIGHT | About 12.6 cm | About 13.5 cm |
| LATERAL BRANCH LENGTH | About 6 cm | About 7 cm |
| LATERAL BRANCH DIAMETER | About 6 mm | about 4 mm |
| STEM COLOR | 144C | 144D with 183D near nodes |
| QUANTITY OF LEAVES PER LATERAL BRANCH | About 9 | About 11 |
| LEAF LENGTH | About 9 cm | About 8 cm |
| LEAF WIDTH | About 3.2 cm | About 3.3 cm |
| LEAF COLOR, UPPER SURFACE | 137A | 139A |
| LEAF COLOR, LOWER SURFACE | 147B | 138B |
| LEAF COLOR, UPPER SURFACE UNDER HIGH LIGHT | 137A | 139A at margins, center yellow, 7A |
| LEAF VEIN COLOR, UPPER & LOWER SURFACES | 145C | 144C |
| PETIOLE COLOR | 145C | 144C |
| FLOWER DIAMETER | About 7.5 cm | About 7.2 cm |
| PETAL COLOR, WHEN OPENING, UPPER SURFACE | 40A | 43A/44A |
| PETAL COLOR, WHEN OPENING, LOWER SURFACE | 41B | 47C |
| PETAL COLOR, OPENED, UPPER SURFACE | 40B with 51A at base | 46C |
| PETAL COLOR, OPENED, LOWER SURFACE | 38B | 46D |
| PETAL COLOR, FADING TO | 39A | 47C |
| PEDUNCLE LENGTH | About 5.6 cm | About 4.5 cm |
| FLOWER BUD COLOR | 41B | 47D |

It is claimed:

1. A new and distinct cultivar of New Guinea Impatiens plant named 'BFP-796', as illustrated and described.

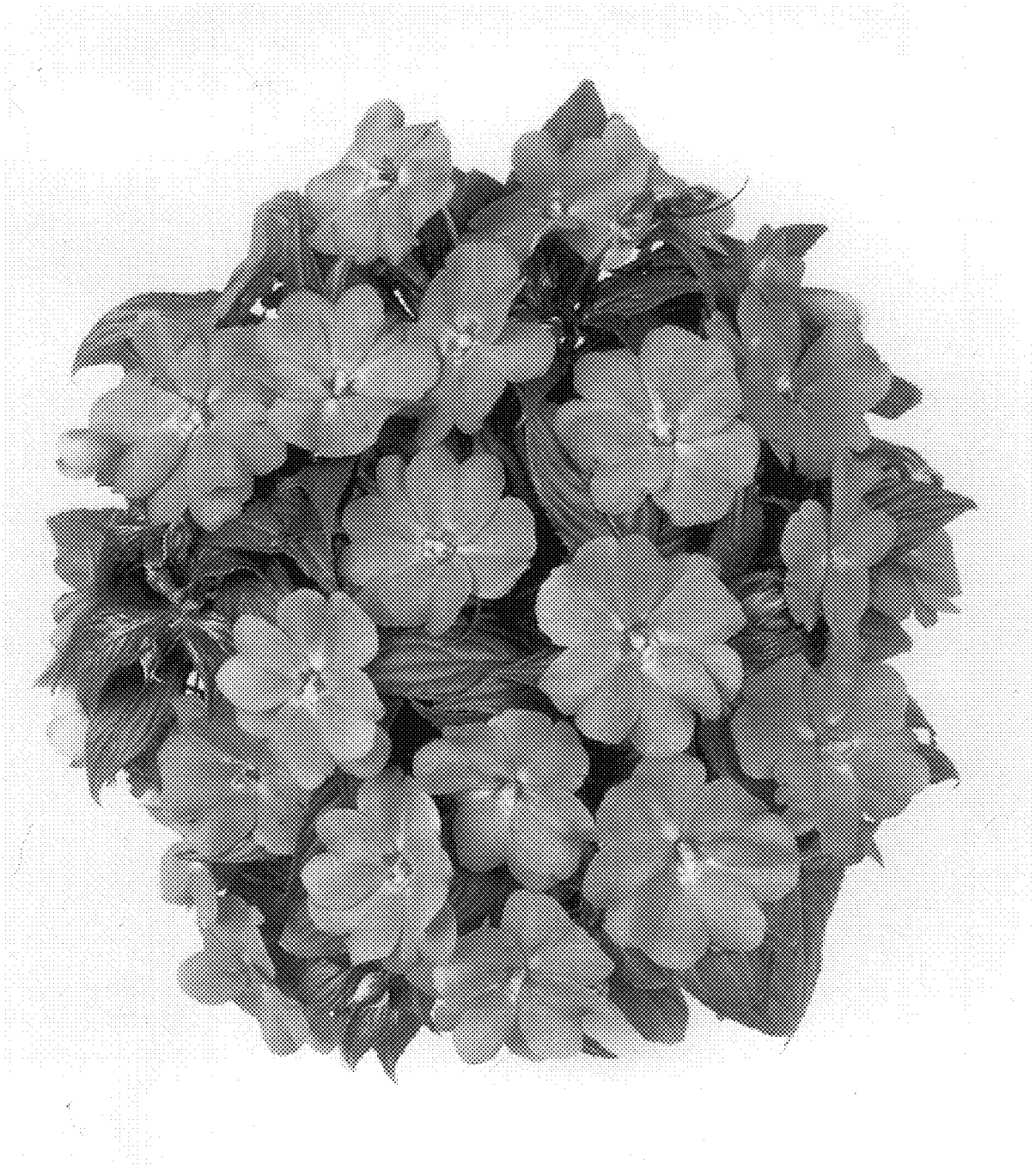

* * * * *